United States Patent

Gray

[11] Patent Number: 5,269,774
[45] Date of Patent: Dec. 14, 1993

[54] IMPLANTIVE OSTOMY RING

[76] Inventor: Michael W. Gray, 1120 N. LaSalle St., Apt. 14-A, Chicago, Ill. 60610

[21] Appl. No.: 951,408

[22] Filed: Sep. 25, 1992

[51] Int. Cl.$^5$ ............................................. A61F 5/44
[52] U.S. Cl. ................................. 604/343; 604/332; 604/338; 604/339; 604/342; 623/11
[58] Field of Search ............. 128/D25; 604/332, 337, 604/338-339, 341-344; 623/11

[56] References Cited

U.S. PATENT DOCUMENTS

| | | | |
|---|---|---|---|
| 3,216,420 | 11/1965 | Smith et al. | 125/D25 |
| 3,570,490 | 3/1971 | Berger. | |
| 3,804,093 | 4/1974 | Fell. | |
| 4,183,357 | 1/1980 | Bentley et al. | 604/339 |
| 4,265,244 | 5/1981 | Hill. | |
| 4,344,434 | 8/1982 | Robertson. | |
| 4,411,659 | 10/1983 | Jensen et al. | |
| 4,518,388 | 5/1985 | Jensen. | |
| 4,534,760 | 8/1985 | Raible. | |
| 4,721,508 | 1/1988 | Burton. | |
| 4,854,316 | 8/1989 | Davis | 604/337 |
| 5,071,407 | 12/1991 | Termin et al. | |
| 5,125,916 | 6/1992 | Panebianco et al. | |
| 5,219,361 | 6/1993 | Von Recum et al. | 623/11 |

FOREIGN PATENT DOCUMENTS

| | | | |
|---|---|---|---|
| 0251502 | 1/1988 | European Pat. Off. | 604/332 |
| 8705796 | 10/1987 | PCT Int'l Appl. | |

OTHER PUBLICATIONS

Selecting Synthetic Mesh for the Repair of Groin Hernia, by Parvis K. Amid, Alex G. Shulman and Irving L. Lightenstein, Postgraduate General Surgery, Apr. 1992.

Primary Examiner—Randall L. Green
Assistant Examiner—A. Zuttarelli
Attorney, Agent, or Firm—Welsh & Katz, Ltd.

[57] ABSTRACT

An ostomy appliance having a ring portion and a sheath portion. The ring portion has a first side, a second side and an aperture substantially centered through the first side and the second side. The ring portion also includes a flange extending radially outward from the aperture. A collection pouch can be removably attached to the first side of the ring portion. A generally cylindrically shaped sheath portion has one end securely attached to the ring portion and a second end. The sheath includes a channel configured to accept the body passage through to the aperture on the ring portion. The sheath is made of a nonabsorbable, noncorrosive mesh material which allows the naturally occurring scaring process of the patient to fibrotically attach the sheath to the body passage, and thereby fixedly secure the ring portion to a substantially permanent location on the surface of the patient's body from within the patient's body.

7 Claims, 6 Drawing Sheets

IMPLANTIVE OSTOMY RING

The present invention relates generally to medical appliances for ostomies, and more particularly, to an implantive ostomy ring intended for use by patients having had an ileostomy, colostomy or other similar surgical procedure.

BACKGROUND OF THE INVENTION

There are many situations in which it is necessary to perform an ileostomy, colostomy, or other similar enterostomy on a patient. Typically, an enterostomy involves externalizing an internal vessel, such as the duodenum, jejunum, ileum, colon, or ureter. The commonly practiced enterostomy involves severing the particular vessel which is to be externalized and then suturing the wall of the vessel to an opening which has been formed on the surface of the body. The vessel which is extended out of the patient's body is generally referred to medically as the "stoma". Typically, the opening is formed through the patient's abdomen.

Following the typical enterostomy an appliance is attached to the patient. The typical appliance comprises an ostomy bag or collection pouch, a connecting ring and faceplate which is glued to the skin surrounding the stoma. This serves to collect waste matter as it is discharged by the externalized vessel. An appliance, according to medical dictionaries, is a device affixed to or implanted in the body and designed to take the place of or perform the function of a missing body part. Often an appliance of a patient exchanges a part of the body for a functional device. There are two classes of appliances: permanent and temporary. Temporary appliances are disposable pouches or wafers, used postoperatively until the stoma has sufficiently healed and a permanent appliance has been selected. In general, permanent appliances are those which can be cleaned and reused. A permanent faceplate may accommodate either a temporary or a permanent pouch. Appliances are manufactured in various sizes to accommodate anatomic variances of patients—newborn, pediatric, regular, and extra large sizes.

Over the past 20 years, much energy has been spent on and vast improvements have been made in ostomy appliances. At present, the variety of equipment available to ostomy patients is bewildering to all but the few experts who take a special interest in this field. With very few exceptions, ostomy patients today use an adherent appliance which in essence is composed of a flat faceplate adhered tightly to the peristomal skin and through the center of which the stoma projects into a pouch that collects the excrements.

The patient who undergoes an ostomy operation has no control over the passage of body wasted materials, liquids, or gases through the intestine or other vessel to the stoma. In the past, pads or adhesively secured receiving ports or faceplates have been used together with a collection receptacle, such as an ostomy bag, and have been taped or adhesively secured over the opening or attached to the stoma by a belt around the body in order to cover the stoma and thereby collect the escape of body waste, liquids, and gases. The known, currently used ostomy devices are inefficient, ineffective, and often lead to embarrassing situations.

The pouches commonly have openings or mouths that are adhesively secured to the skin or connected around the stoma via the faceplate having an ostomy ring. The pouches must be periodically removed and emptied after body excrements have been collected therein. It is important that the adhesive seal between the mouth of the bag and the faceplate and the skin surrounding the stoma be maintained airtight to prevent the escape of embarrassing odors or the leakage of body excrement. All too often with currently available appliances, the patient may suffer painful irritation and serious infection when the area between the adhesive seal and the skin breaks down and comes in contact with bodily excrement.

Typical ports, or faceplates, require the user to adhere the underside of the plate to the skin surrounding the stoma. Although faceplates come in numerous styles and materials, they are not able to ensure a completely tight, leak-proof seal around the stoma. Additionally, it is common that the ostomy patient will suffer pain or great discomfort when attaching or reattaching the pouch, because it is normally necessary to apply some force to engage or disengage the coupling elements. Further, ostomy patients are normally required to remove the faceplate and clean the area every three to five days. The procedure involved in removing and reattaching the faceplate is time consuming and can cause serious skin irritations, which can then lead to serious infections.

The currently available ostomy appliances include a number of accessories that become costly and tend to complicate the ostomy patient's life. These accessories include: Stomahesive, reliaseal, and karaya disks used as gaskets. Karaya gum powder or paste is used as a protective base, allowing the skin to heal. A karaya gum washer may be stretched or cut to fit snugly around the stoma. Very thin, double-faced adhesive disks are used to adhere the faceplate and appliance to the skin and are often used instead of cement. Solvents may be used to dissolve cement and adhesives and are necessary for removing the appliance. A noncaustic oil base solvent is available for those with tender skin. Telfa ® may be used when the skin becomes irritated. Telfa ® is a sterile, nonadhering dressing that allows excoriated skin to heal without further damage. Micropore, a paper tape, is a nonallergenic tape for those who are unable to use adhesive tape. Stoma bibs made of diaper cloth or cotton flannel fit under the plastic pouch to absorb perspiration and keep the appliance from contacting the skin. O-rings, made of covered elastic thread, may be stretched slightly to fit around the disk to secure the pouch. Rubber rings or plastic valve sets may be utilized as pouch closures.

Currently an ostomy patient must not only learn to use all the accessories and deal with the inconveniences and uncomfortable situations involved in having an ostomy bag appliance, but must continually, almost obsessively, deal with the cleaning, changing and administering of the appliance. Further, the currently available faceplates not only cause irritation to the skin upon being changed or removed, but as the faceplate loosens from the skin during normal human activity, fecal matter can contact and collect on the irritated skin area and cause serious infection and further discomfort to the patient. When skin irritations or infections do result, the patient is often required to expend additional time and money to treat the problem, which may require expensive antibiotics or even admittance to a hospital.

The use of adhesively secured faceplates can create great discomfort and even dangerous infections to the ostomy patient. Accordingly, not only does the patient have to deal with the stresses of maintaining the ostomy device, but must also be concerned with embarrassing and harmful leakage of the excrement between the stoma and the faceplate. Typically, these faceplates work effectively for a limited time period. After the user has repeatedly attached, and removed the pouch from the faceplate, the faceplate may begin to separate from the skin, thereby allowing excrement to leak. In attempting to prevent the leakage, patients have been known to use duct tape, dangerous adhesive solutions, or other less than satisfactory ways to solve the problem of leakage from between the faceplate and the patient's skin. Such homemade remedies are only temporary solutions and often lead to even more serious infections and discomfort.

For every ostomy patient, there exists the everpresent possibility of skin irritation. The most common cause of skin problems to the ostomy patient is leakage under the faceplate of the appliance. Whenever excrement comes into direct contact with the skin, irritation develops and very soon excoriation and intense inflammation supervenes. skin damage may arise from too frequent changing of the appliance, excessive use of adhesive remover, or too vigorous scrubbing or drying of the peristomal area. Monilial infection can also occur under the faceplate, where it can be difficult to distinguish from other forms of skin irritation.

There have been some attempts to provide an ostomy device which prevents leakage and which lasts for a longer period of time without the required maintenance. However, some of these medical devices require extensive dissection or additional operative steps in order to internally mount the ostomy ring to the patient's body. Further, currently known and available implantive type ostomy rings, require that the vessel, such as the colon, be drawn over the artificial passageway and terminate at approximately the surface of the skin. The technique of feeding the device into the vessel to provide an exterior port for the attachment of a collection pouch may cause hemorrhaging or serious infection, such as sepsis, due to irritation between the vessel and the tube and the internal leakage of fecal matter which may go into the blood stream and cause toxic sepsis.

Thus, there is a need for an ostomy appliance which can be easily adapted to currently practiced methods of performing ostomies. There is also a need for an ostomy appliance which is easily implanted into the patient's body during the ostomy procedure, and which provides the patient with an easy to use and fairly permanent port, or ostomy ring, to which a collection bag can be repeatedly attached and removed without irritation to the patient's skin or harmful and unpleasant leakage of excrement from the ostomy appliance. Further, there is a need to provide a low maintenance ostomy appliance having an internal securing or anchoring system, which utilizes the patient's naturally occurring fibrotic reaction (scar formation) to attach the ostomy ring securely to the patient's body without the need of adhesives and an exteriorly mounted faceplate.

Accordingly, it is an object of the present invention to provide an ostomy appliance which is partially implanted into the ostomy patient's body and through the patient's naturally occurring fibrosis is anchored to the body, thereby fixing the ostomy ring on the exterior of the patient's body.

It is yet another object of the present invention to provide an ostomy appliance which is readily incorporated into currently practiced enterostomy surgical procedures without requiring any additional surgical steps or additional dissection of the patient's body.

It is yet a further object of the present invention to provide a low maintenance ostomy appliance which is implanted within the patient's body, provides a fixed ostomy ring which eliminates leakage, minimizing the risk of infection and effectively reducing the amount of maintenance required by the patient.

SUMMARY OF THE INVENTION

In accordance with the present invention, all of these objects, as well as others not herein specifically identified, are achieved generally by the present implantive ostomy ring including a faceplate or ring portion having one side configured to releasably accept a waste collection bag and a second side. The faceplate includes an aperture through which the externalized vessel is extended and a flange which gives backing support to the ring portion.

A sheath formed of a nonabsorbable, synthetic mesh includes a channel through which the vessel is extended through the aperture and out of the patient's abdomen. The sheath is integral with or secured to the second side of the faceplate. The sheath is configured to allow fluid to pass between the patient's vessel and the sheath, and which allows the patient's naturally occurring scarring processes to fibrotically secure the faceplate from within the patient's body. The sheath extends from the second, or underside of the ring portion and has a sufficient length for application to a broad range of patients and vessel types. The sheath may include a reinforcing filament woven through the material that may or may not be integral with the underside of the ring portion.

BRIEF DESCRIPTION OF THE DRAWINGS

Further objects of the invention, together with additional features contributing thereto and advantages occurring therefrom, will be apparent from the following description of the invention when read in conjunction with the accompanying drawings, wherein.

DETAILED DESCRIPTION OF THE INVENTION

Figure 1:
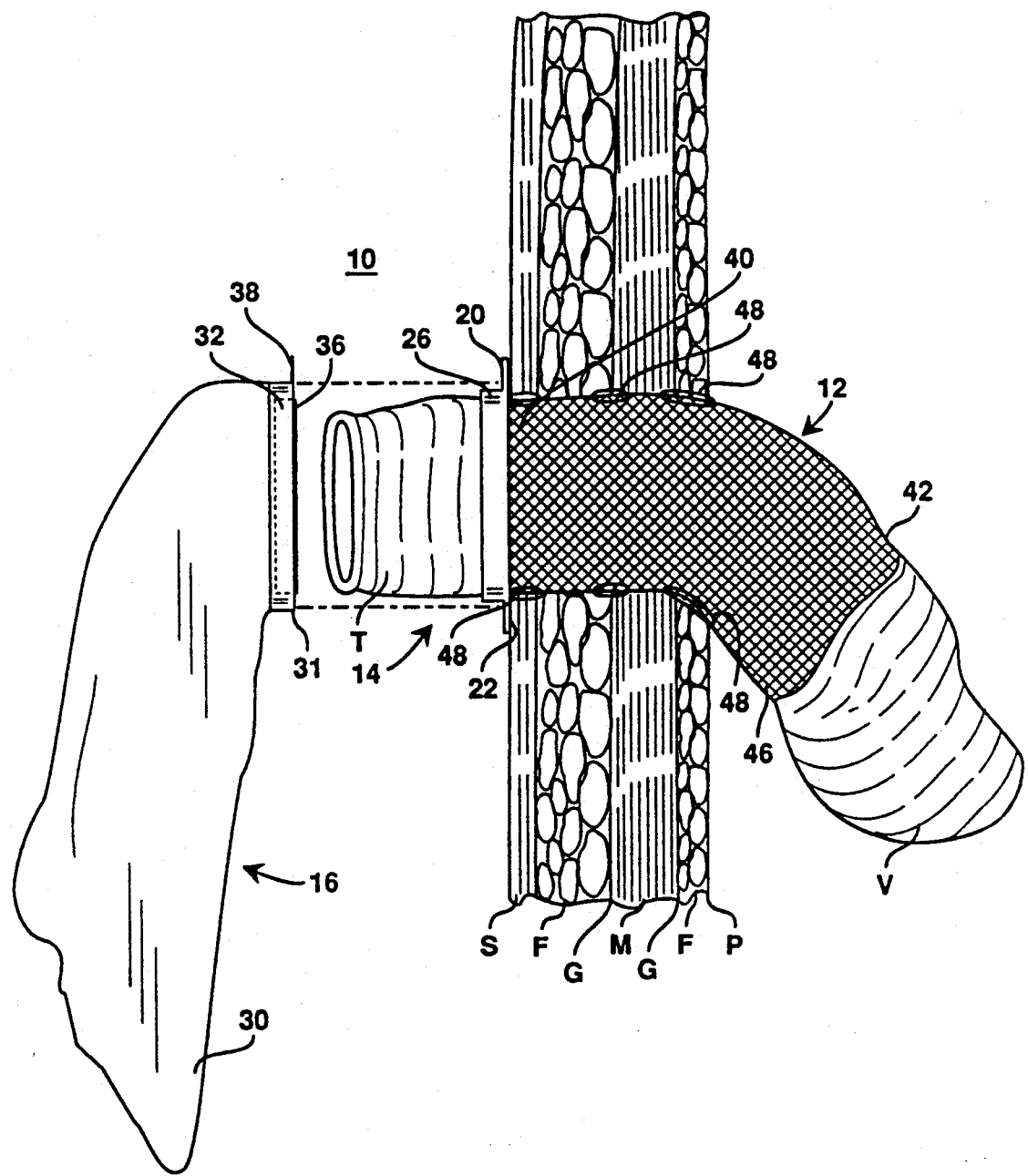
FIG. 1 depicts a side view of the present implantive ostomy ring invention attached to the patient and an ostomy bag shown detached from the ring.

Referring first to FIG. 1, the implantive ostomy ring is designated generally as 10, and includes a sheath portion 12 and a ring portion 14. The ring portion 14 is also known as the faceplate of the ostomy appliance. Also shown in FIG. 1 is a typical ostomy bag 16. Through the several figures, "S" represents the patient's skin, "F" and "M" refers respectively to layers of fat and muscle, "G" refers to the layers of fascia and "P" refers to the peritoneal cavity. "T" refers to the stoma of the externalized vessel "V", which extends out of the patient's abdominal wall. The vessel "V" or body passage will typically be the patient's large or small intestine. However, it should be understood that the principles set forth by the present invention are applicable to other body passages that are externalized or applicable to enterostomy procedures.

The faceplate or ring portion 14 includes a first, or outer surface 20, a second, or inner surface 22 and a generally circular aperture 24 that extends through surfaces 20 and 22. The outer surface 20 is a substantially flat surface from which an integral lip 26 outwardly extends, and which is used to connect the ring 14 to the ostomy bag 16 or other collection apparatus. This outwardly extending integral lip 26 can also be configured with other known connection devices, such as typically available screw type threading (shown in FIG. 5). However, for ease of use it is preferred that the ostomy bag 16 is snapped onto the ring 14 using the lip 26.

In contrast, the inner surface 22 is substantially flat without having any projections, indentations or deformations. The inner surface 22 is preferably flat in order to cause the ring to lie relatively flush upon the patient's abdominal skin. Nevertheless, it is contemplated that other configurations for the inner surface 22 may be utilized, such as a slightly concave surface, in certain situations in order to further decrease any distances between the ring 14 and the patient's skin surface.

The outer surface 20 and inner surface 22 essentially form a flange 28, which provides a support surface upon which the integral lip 26 or other connection device is formed. The flange 28 should be dimensioned to give the lip 26 or other closure device sufficient structure and backing for mounting the ring onto the patient's abdomen. However, it should be understood that the flange 28 should be configured to stabilize the desired connector for attachment or removal of the bag 16 to the ring 14 and to minimize the risk that the ring 14 will be pulled out from the patient's body. It is preferred that the flange 28 be somewhat small in diameter in order to minimize the collection of moisture, bacteria or dirt between the ring 14 and the patient's skin surface, and to minimize the risk of painful removal of the ring 14 if the patient attempts to clean or dry the area underneath the flange 28.

The ring 14 can be made of any suitable material which is nontoxic, noncorrosive, lightweight and preferably inexpensive. To limit the risk of an adverse reaction or rashes which can occur between the ring 14 and the patient's skin, it is preferred that plastic or noncorrosive, noneroding, lightweight metallic substances be used in manufacturing the ring 14. The material chosen will not detract from the scope of the present invention.

Figure 2:
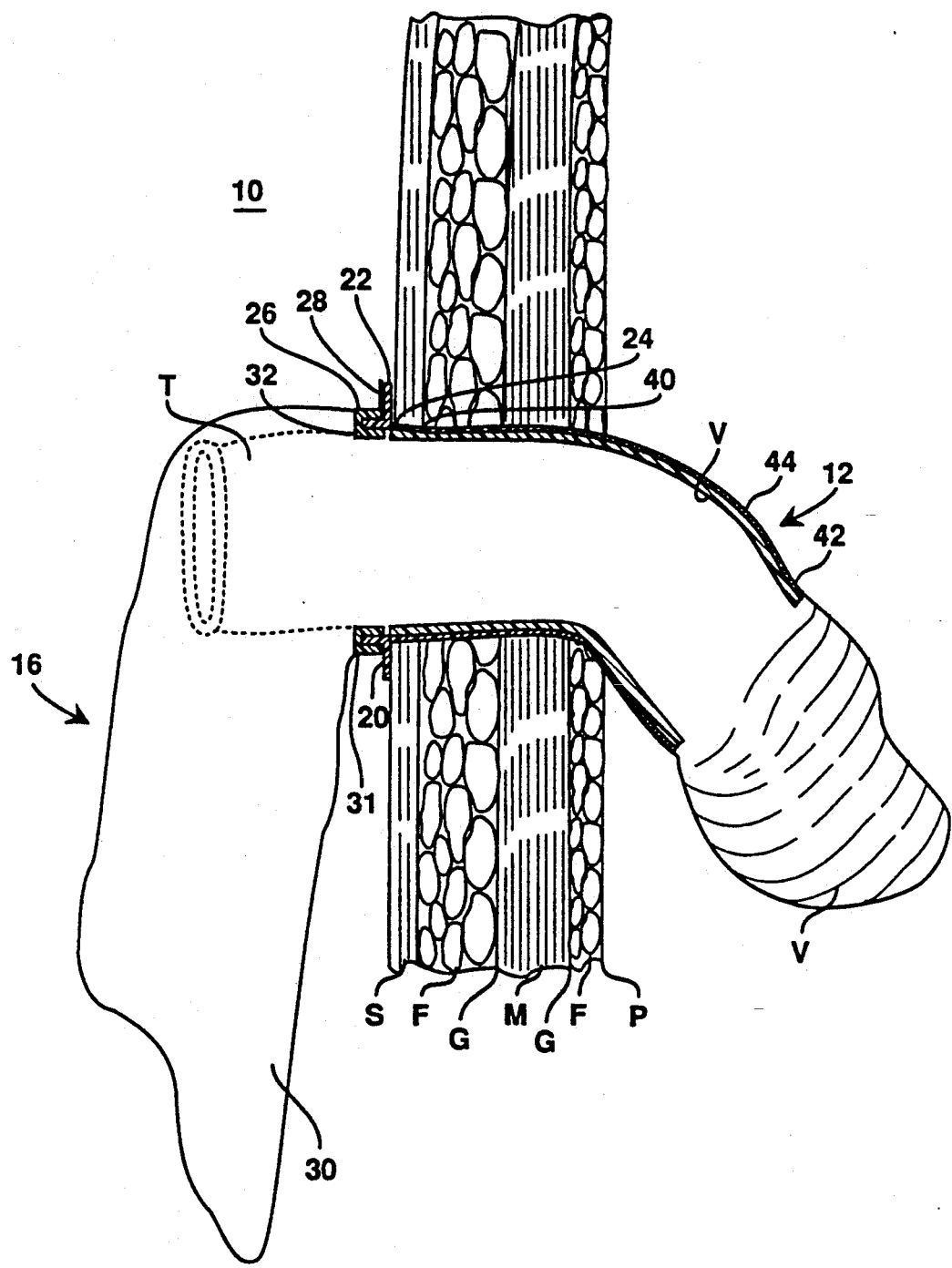
FIG. 2 depicts a cross sectional view of the present implantive ostomy ring with the ostomy bag attached to the ring.
Figure 6:
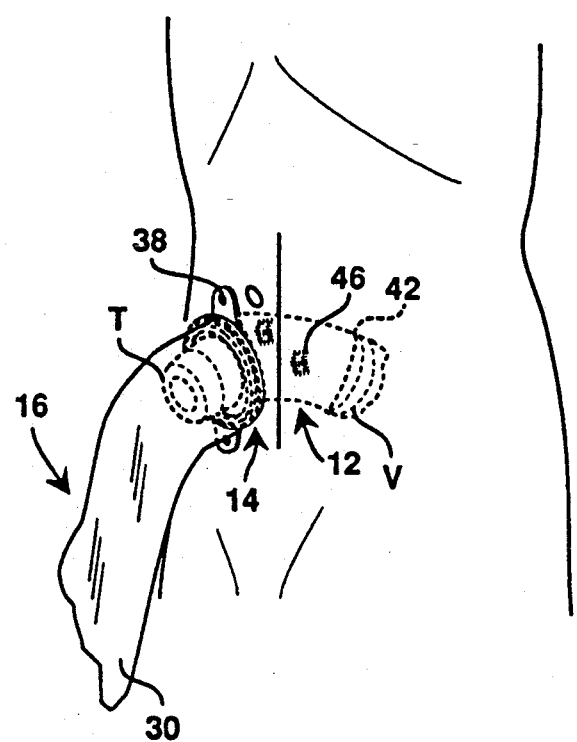
FIG. 6 depicts the present implantive ostomy ring and an ostomy bag fully attached to a patient.

The ring 14 is designed to act as a port for the connection of the ostomy bag 16 over the stoma of the externalized vessel (FIGS. 2 and 6). Accordingly, the opening 24 must be large enough to accommodate the stoma extending out of the patient's abdominal wall without any unnecessary irritation to the vessel walls. The inner surface 22 of the ring 14 should rest relatively flush on the patient's skin once the present implantive ostomy ring has been secured within the patient's body. As shown in FIG. 6, the stoma of the externalized vessel will extend out of the abdominal wall and through the opening 24 until it extends sufficiently from the patient's body for the proper discharging of the patient's waste matter into the ostomy bag 16. Therefore, the configuration of the opening 24 will depend on the vessel being externalized from the patient. It is preferred that the opening 24 be generally circular in configuration, having a diameter which generally coincides with the diameter of the externalized vessel in order to prevent leakage from the patient's body or foreign matter from entering the patient's body. Accordingly, the present implantive ostomy ring 10 can be configured with an unlimited number of opening configurations so as to properly match the patient's specific vessel being externalized.

Figure 3:
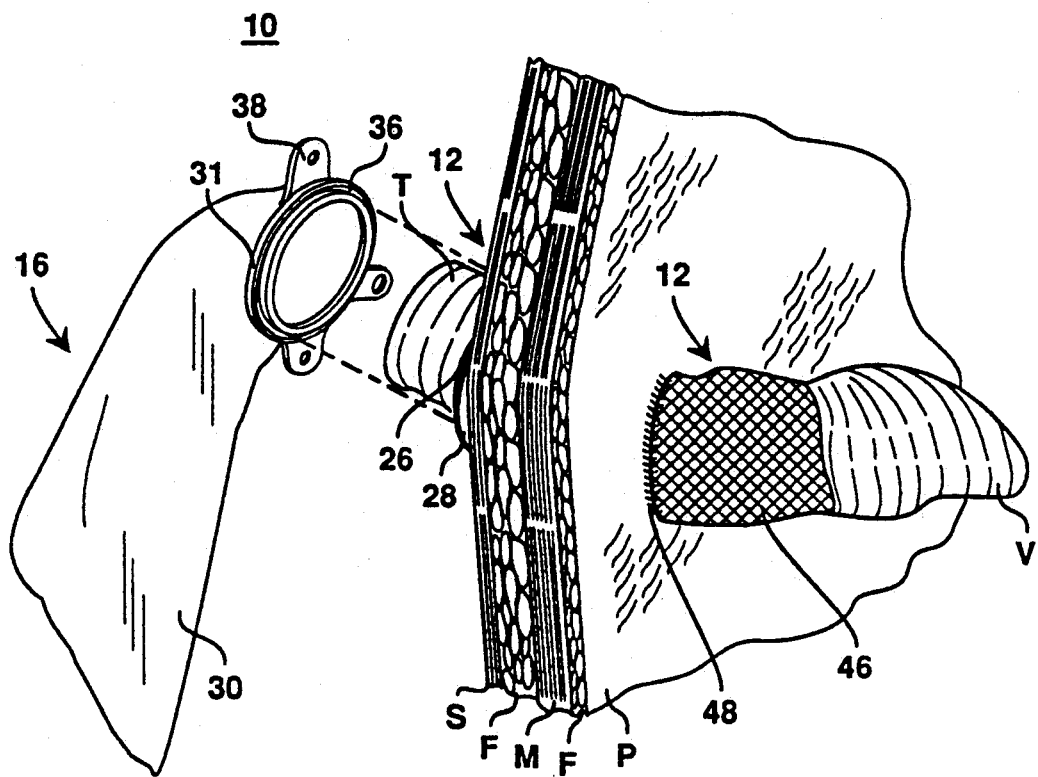
FIG. 3 depicts a side perspective view of the present implantive ostomy ring attached within the patient's body.
Figure 4:
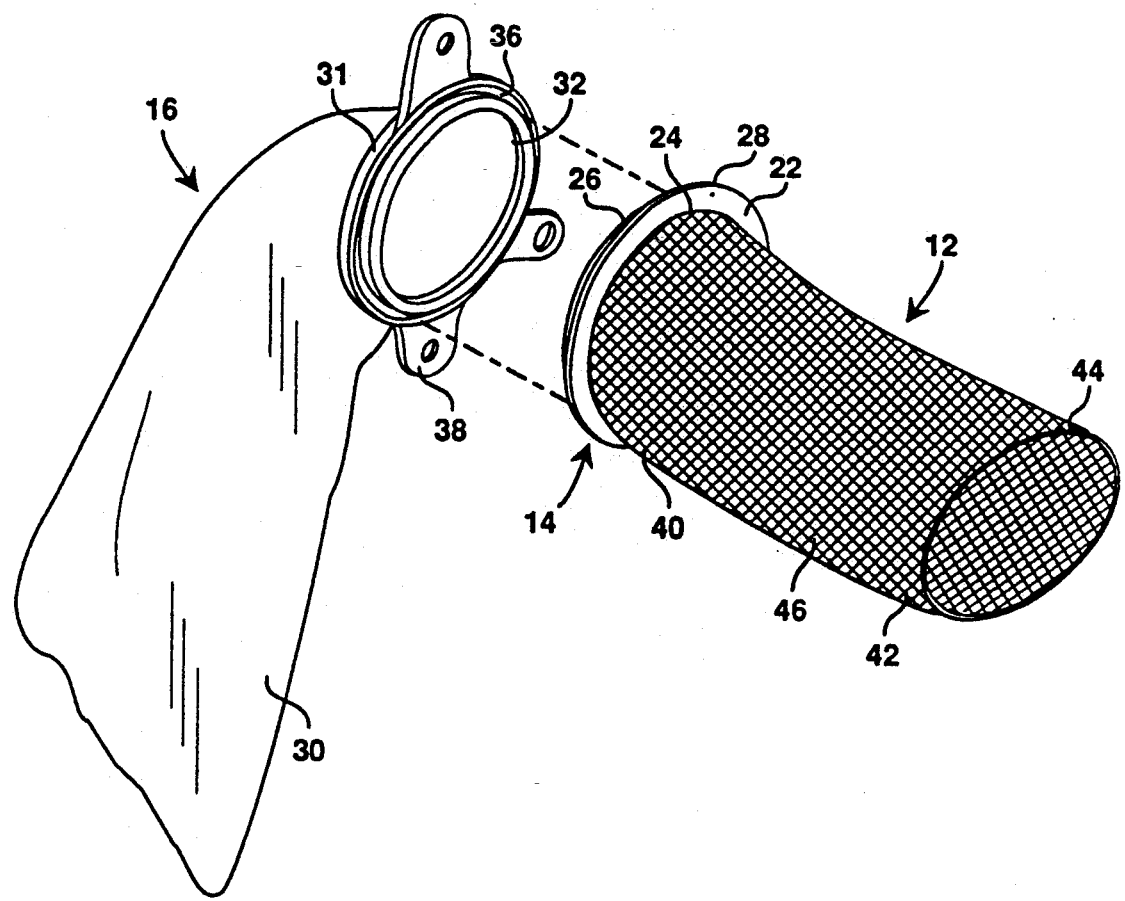
FIG. 4 depicts a side perspective view of the present implantive ostomy ring apart from the patient's body and apart from the ostomy bag.
Figure 5:
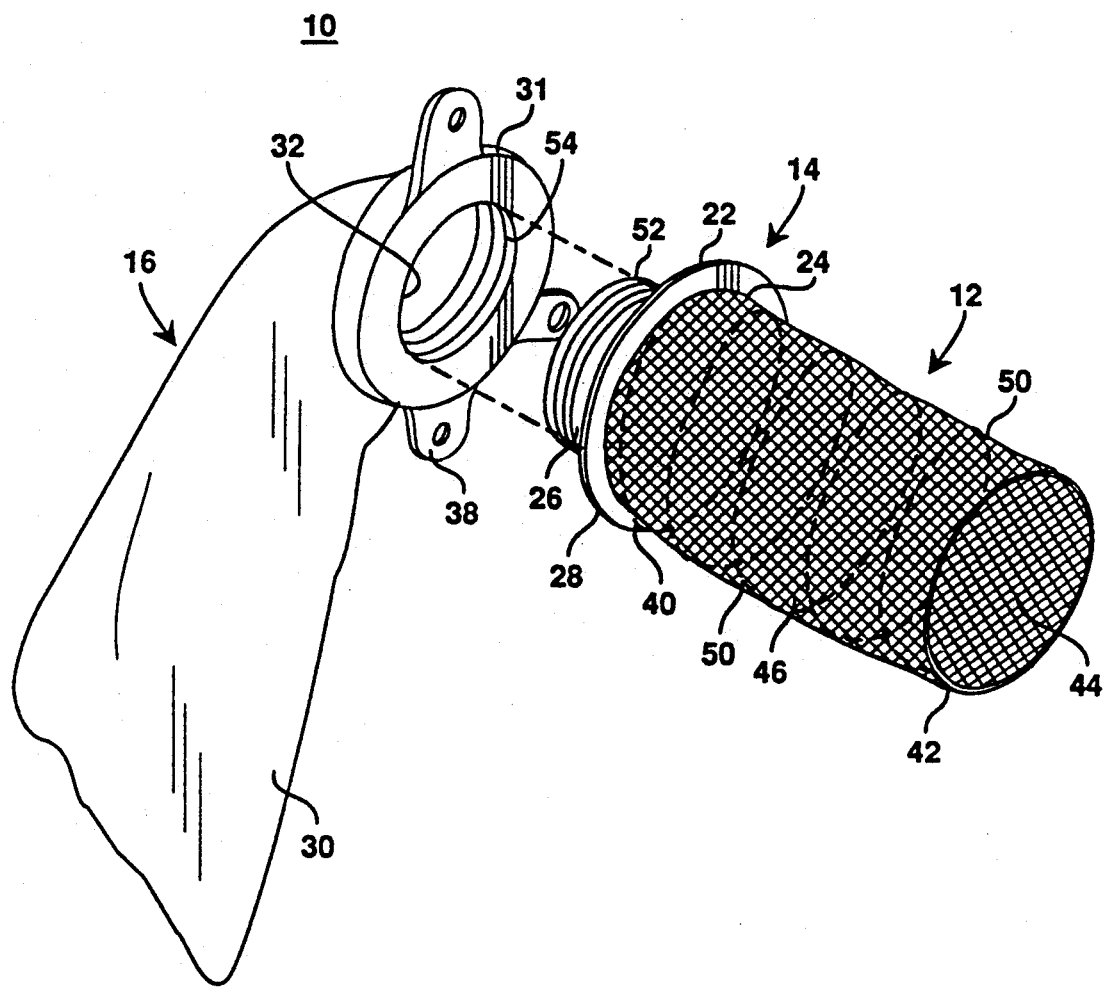
FIG. 5 depicts an alternative configuration of the present implantive ostomy ring.

Referring to FIGS. 4 and 5, an ostomy bag, such as bag 16, is typically utilized to collect the waste matter discharged from the patient's body. The ostomy bag 16 typically includes a bag portion or a collection pouch 30 having an inlet plate 31 with an opening 32 through which the waste matter is discharged into the bag 16 by the patient having had the enterostomy. The ostomy bag 16 will also usually include along the perimeter of the opening 32, a connector 36 which is configured to matingly engage the connector, such as lip 26, on the ring 14. It should be understood that the ostomy bag 16 can be configured with different formations of connectors (grooves, slots, screws, projections, etc.), as long as the formation is complimentary to the connector utilized on the ring 14. As depicted in FIG. 1, the preferred connector 36 is configured as a receiving channel that securely accepts the lip 26 on the ring 14 and maintains a secure attachment until the patient pulls the bag from the ring 14. As can be best seen in FIG. 3, the ostomy bag 16 may include at least one gripping formation 38 to facilitate removal of the ostomy bag 16 from the ring 14, typically by lightly peeling the connector 36 away from the lip 26.

Referring to FIG. 4, the implantive ostomy ring 10 also includes a sheath 12, which extends away from the inner surface 22 of the ring 14. The sheath has a first end 40 and a second end 42. The sheath 12 can be separately manufactured and then connected to the inner surface 22 of the ring 14, or alternatively can be integrally formed along with the ring 14. Further, it is preferred that the sheath 12 be of a unitary construction. However, it is contemplated by the present invention, that the sheath 12 could be split in half or other portions for customization by the surgeon utilizing the present implantive ostomy ring 10.

As shown in FIGS. 2 and 4, the sheath 12 is generally tubular and includes a channel 44 which extends from the first end 40 through the second end 42. The channel 44 of the sheath 12 is generally in alignment with the opening 24 of the ring 14. The sheath 12 is preferably a lightly porous biomaterial. As shown throughout the figures, the sheath 12 has mesh-like formations 46. The material used must be such that the patient's body will not reject, deteriorate or absorb it. The material must be strong enough to withstand the body's deteriorative substances, yet flexible enough to conform with the patient's vessel. The length of the sheath 12 and the width of the channel 44 can be selected by the surgeon in order to accommodate the specific size of the vessel being externalized as well as the dimensions of the patient's own particular layers of fat and muscle. Accordingly, it is contemplated that the sheath 12 will actually be manufactured of a length and width having dimensions broad enough to allow for the application of the present implantive ostomy ring 10 to a wide range of vessels and patient types. Therefore, it should be understood that the present implantive ostomy ring 10 will fit a wide range of uses, and can be manufactured such that the surgeon can tailor the sheath 12 to fit the particular patient.

The surgeon can customize the sheath 12 by reducing its length and/or by cutting or folding the sheath 12 in order to create the necessary dimensions for the specific patient. Because of the resiliency caused by the mesh formations 46, the sheath 12 can be folded over upon itself, stretched or otherwise manipulated to fit the specific patient's needs without disrupting the objectives of the present implantive ostomy ring 10. Although the sheath 12 is shown as tubular, it is contemplated that the present implantive ostomy ring 10 can be delivered to the surgeon with the sheath 12 connected to the inner surface of the ring 14, yet opened along the length of the sheath 12. In this way, the surgeon can simply form a conduit, such as channel 44 of sheath 12, having a desired width and secure the sheath 12 together into a tubular or otherwise required configuration.

To keep the cost of the present implantive ostomy ring 10 at a minimum, it is preferred that the material utilized for the sheath 12 be inexpensive and easily available. The material will preferably have sufficient porosity to allow fluids to pass through the material. Currently available and acceptable biomaterials are tantalum mesh, stainless steel mesh, polyester cloth (Dacron®), polyester sheeting (Mylar®), nylon mesh, Dacron® mesh (Mersilene®), acrylic cloth (Orlon®), polytetrafluroethylene, which is Teflon® mesh and cloth, and polypropylene mesh (Marlex® and Prolene®). Marlex® is preferred due to its mesh size and availability. This is not meant to be an exhaustive list of available materials, but only an indication of the type of materials that can be utilized for constructing the sheath 12 pursuant to the present implantive ostomy ring 10.

Regardless of the material chosen, it must be understood that the preferred material is nonabsorbable and has a sufficiently large mesh formation 46 to allow the patient's body to form scar tissue (the naturally occurring fibrotic reaction) around and through the sheath 12. Although it is contemplated that the entire sheath 12 need not be porous or mesh, it is preferred that the entire sheath 12 be porous so that the patient's body will attach itself to the length of the sheath 12 for a more secure attachment into the patient's body. It is contemplated that most available biomaterials with a mesh size of at least 10 microns will work to attach the ring 14 to the patient. However, although other dimensions of the mesh formations 46 will work sufficiently, it is preferred that the mesh material be 750 microns * 600 microns, or at least between 600 and 750 microns wide. It is contemplated that the sheath 12 can be formed of a material having no measurable porosity or porosity of less than 10 microns, which would only allow fibrotic attachment to occur separately on the exterior and the interior surfaces of the material and not through the material.

Presently available implantive ostomy appliances utilize a tube-like structure around which the vessel is extended and drawn over. In contrast, as shown best in FIG. 2, the present ostomy ring 10 effectively anchors the ring 14 to the abdominal wall by extending the vessel through the channel 44. Once the surgeon has completed all the surgical steps involved in separating the vessel to be externalized, the surgeon feeds the vessel through the channel 44 of the sheath 12. Once the vessel has been extended through the channel 44, the sheath 12 is then surgically secured, such as by sutures 48, to the vessel and the surrounding layers of fat, muscle, fascia or peritoneum.

As shown most clearly in FIGS. 1 and 3, the preferred method of securing the sheath 12 is by extending the stitches or sutures 48 through the mesh formations 46 into and through the vessel being externalized and through the various layers of the patient's abdominal wall. As shown in FIG. 1, a set of sutures 48 is extended through the skin, at the uppermost end, another set is extended through the muscle and fascia at about a midway point within the patient's body, and a third set is extended through the peritoneum and muscle at a lower portion just above the peritoneal cavity within the patient's body. These sutures 48 are preferably absorbable, but nonabsorbable suturing material may be used to more securely attach the ring 14 to the patient's body.

Referring again to FIG. 2, the implantive ostomy ring 10 is shown in cross section, and depicts how the vessel extends through the patient's layers of fat, muscle, fascia and peritoneum and out of the abdominal wall. More particularly, the externalized portion of the vessel, referred to as the stoma, extends beyond the ring 14 and into the bag 16 to foster proper discharge of the waste material into the collection pouch 30. As shown, the lip 26 of the ring 14 is matingly engaged to the connector 36 of the ostomy bag 16. This connection should be airtight to prevent the escape of unpleasant odors resulting from the waste matter and to prevent harmful and destructive leakage of the waste matter onto the patient's body or skin. As shown in FIG. 21 the sheath 12 envelops the vessel and extends from a point immediately below the inner surface 22 of the ring 14 through the several layers and into the peritoneal cavity. Although not required, it is preferred that the sheath 12 envelop the vessel and extend at least into a small portion of the peritoneal cavity to promote a stronger attachment of the ring 14 onto the patient's abdominal surface.

Once the sutures 48 are absorbed by the body, the mesh formations 46 will have allowed the vessel to fibrotically attach itself to the sheath 12 using the body's natural scaring processes. The mesh formations 46 also allow the escape of fluids from between the vessel and the sheath 12, so as to promote the healing and scaring of the incision around and through the sheath 12. Accordingly, the present implantive ostomy ring should become a fairly permanent fixture of the patient's body once the body's fibrosis or scaring process has worked its way in and through the mesh-like formations 46 of the sheath 12. Additionally, because the vessel is extended through the channel 44 of sheath 12 and attached to the sheath 12 up to the skin surface, it is unlikely that bodily fluids or waste will leak between or around the stoma and inner surface 22 of the ring 14. The patient's body essentially seals the gap between the stoma and the ring 14 without the use of washers or adhesives. Also, because the patient's scaring process will seal any gaps between the ring 14 and the patient's body, there is less risk of foreign matter or waste matter contacting the patient's body and causing serious infection or disease.

More particularly, in FIG. 2 it is shown how the sheath 12 extends or envelops the externalized vessel from a point directly below the patient's skin surface down through the many layers of the abdominal wall and into a portion of the peritoneum cavity. As is shown in FIG. 2, the vessel is extended through the channel 44 of the sheath 12 and out the abdominal wall of the patient. Once the patient's body has been given time to heal, the present implantive ostomy ring 10 will provide a substantially leak proof and infection free environment for the ostomy patient. Further, because the sheath 12 permanently attaches the ring 14 to the patient's body from within the patient's body, there is no need to use adhesives or pastes to secure or seal the ring 14 around the stoma. Also, in FIG. 2 the inner surface 22 of the ring 14 is shown generally flush with or resting upon the patient's abdominal skin surface. It is preferred that the ring 14 sit generally flush with the patient's skin surface to minimize the accumulation of dirt and perspiration in between the inner surface 22 or flange 28 and the skin surface.

Referring now to FIG. 3, the sheath 12 has been secured to the exterior of the vessel and through layers of fat, muscle, and fascia and into the peritoneal cavity. The sutures 48 have been applied to temporarily attach the implantive ostomy ring 10 within the patient's body until the body's own scaring process causes the vessel to attach to the sheath 12. It should be understood that in initially attaching the implantive ostomy ring 10 within the patient's body, the surgeon is not required to make additional incisions or add complicated steps to currently practical ostomy procedures. In other words, the present invention can be directly merged into presently practiced procedures. This also benefits the patient because recovery time is shortened since there are no additional incisions to suture or allow to heal and less risk of infection.

Referring now to FIG. 5, there is shown various alternative features of the present implantive ostomy ring 10. In order to provide a reinforcing structure to the sheath 12, at least one nonabsorbable, reinforcing filament 50 can be incorporated or woven through the mesh-like formations 46. More specifically, it is preferred that the reinforcing filament 50 extend from the first end 40 of the sheath 12 substantially through to the second end 42 of the sheath 12. Further, it is preferred that the reinforcing filament 50 be made of the same material as the ring portion 14 such that the reinforcing filament 50 can be integrally formed with the ring 14 and extend down through the sheath 12.

As shown in FIG. 5, the reinforcing filament 50 spirals down the length of the sheath 12. However, it is contemplated that the reinforcing filament 50 can be of other lengths and woven through the sheath 12 in numerous other manners such that the sheath 12 is reinforced and such that the sheath 12 will not separate from the ring 14. It is important to realize that the sheath 12 must be securely attached to the ring 14 such that the sheath 12 does not separate from the ring 14 over extended use of the present implantive ostomy ring 10. Accordingly, it is contemplated that a reinforcing filament 50 will be used, or that the sheath 12 will be permanently secured to or integrally formed with the ring 14.

As discussed above and shown in FIG. 5, the collection pouch 30 can be attached to the ring 14 using a variety of connection arrangements, such as complimentary threading 52 and 54. Further, it should be understood that other available connection arrangements can be utilized without departing from the scope of the present invention. Preferably, the attachment will be leak proof and airtight, while still being easily detachable so as to prevent premature separation of the ring 14 from the sheath 12 or painful tearing of the ring from the skin surface.

In FIG. 6, the implantive ostomy ring 10 has been internally secured to the patient's body and is shown providing the externalization of the vessel into the collection pouch 30. As can be seen in FIG. 6, the externalized vessel will typically extend from the patient's abdominal wall and directly into the collection pouch 30. Together with the sealing attachment of the patient's body to the sheath 12, the extension of the stoma further minimizes the possibility of leakage and infection.

In use, the present implantive ostomy ring 10 provides the ostomy patient with a fixedly secured ring 14 that utilizes the patient's own scaring processes to fibrotically attach the ring 14 onto the abdominal wall. In this way, the patient is no longer required to administer the appliance, such as by cleaning, gluing or periodically changing the faceplate. Further, the implantive ostomy ring 10 allows the surgeon performing the enterostomy to attached the ring 14 to the patient's body without additional incisions or operative procedures to the patient. In other words, the surgeon performing the enterostomy can easily adapt presently used operating procedures to include the attachment of the implantive ostomy ring 10 without increasing the complexity of presently utilized surgical procedures.

Once the implantive ostomy ring 10 has been implanted within the patient's body, the patient can function in everyday society without the burden of having to administer the ostomy appliance. Except for periodic pouch cleaning or changing and ordinary bodily hygiene around the stoma, there is no maintenance required. Accordingly, the present implantive ostomy ring 10 promotes the patient's ability to adapt to having an ostomy and the appliance and function quite normally without the ever impending fear of leakage and infection. The patient utilizing the present implantive ostomy ring 10 will no longer need to deal with the constant maintenance of the ostomy appliance, which fosters the patient's ability and confidence to function in everyday society. Because the present implantive ostomy ring 10 does not require constant changing, cleaning and application of adhesives, the ostomy appliance can become virtually unnoticeable and practically invisible fixture.

The present implantive ostomy ring 10 is not only inexpensive to manufacture, but is inexpensive for the patient to have and maintain. Because the present invention does away with the costs associated with the use of adhesives and the obsessive need to clean and maintain the ostomy appliance, it is also less expensive for the patient to maintain. Because adhesives are not used, the problems of irritation and infection attributable to the adhesives, the adhesive removers and other substances are eliminated. Ostomy patients do not have to be concerned with leakage due to creases, folds or separation of the faceplate that develop using currently available appliances, because the faceplate or ring 14 simply sits on the patient's abdomen and is sealed to the patient's body via the sheath 12. The ostomy patient utilizing the present implantive ostomy ring 10 is not burdened with embarrassing and complicated components. Instead, the present ring 10 makes the ostomy virtually invisible both in appearance and to the patient psychologically. It is lightweight, simple to use and fairly maintenance free.

While various embodiments of the present invention have been shown and described, it should be understood that various alternatives, substitutions and equivalents can be used, and that the present invention should only be limited by the claims and equivalents thereof.

Various features of the present invention are set forth in the following claims.

What I claim is:

1. A combination ring and collection pouch for an ostomy, said combination comprising:
   a ring portion having a first side, a second side and an aperture substantially centered through said first side and said second side, said ring portion having a flange integrally formed on said ring portion which extends radially outward from said aperture to provide a support backing to said ring portion;
   means for collecting waste matter from a body passage;
   means for securing said collection means to said first side of said ring portion, said collection means communicating with said body passage through said aperture when said collection means is secured to said ring portion;
   a flexible sheath being of a certain length and having one end securely attached to said second side of said ring portion and a second end, said sheath having a channel for accepting said body passage through to said aperture, said sheath conforming to said body passage throughout said length of said sheath, said sheath allowing naturally occurring scarring process of a patient's body to fibrotically attach said sheath to said body passage and thereby fixedly secure said ring portion to a substantially permanent location on a surface of said patient's body completely from within said patient's body without adhesives; and
   a nonabsorbable filament integral with and depending from said second side of said ring portion, said filament being independent of and extending through said first end of said sheath and terminating substantially at said second end of said sheath for securely attaching said ring portion to said sheath.

2. The combination as defined in claim 1 wherein said sheath is formed entirely of a nonabsorbable mesh material which is substantially porous.

3. The combination as defined in claim 2 wherein said mesh material has pores of between 600 and 750 microns in diameter.

4. The combination as defined in claim 1 wherein said filament is woven in and through said mesh sheath.

5. An ostomy appliance for the collection of bodily fluids from a stoma of a body passage of a patient, said ostomy appliance comprising:
   a faceplate having a first side, a second side and a substantially centered aperture which extends through said first side and said second side, said faceplate having an integral flange which extends radially outward from said aperture to provide a resilient support backing structure for said faceplate;
   said faceplate having means for releasably securing a collection pouch around said aperture;
   a sheath formed of a mesh being of a predetermined length and having a first end and a second end, said first end being securely attached to said second side of said faceplate substantially alongside and around said aperture, said second end of said mesh sheath having a channel for accepting said body passage therethrough, said sheath and said channel generally conforming to said body passage throughout said predetermined length of said sheath; and
   a filament being independent of said mesh sheath and attached at one end to said second side of said faceplate, said filament being interwoven in said mesh and extending substantially said predetermined length of said sheath, said filament providing a secure attachment of said faceplate to said sheath.

6. The ostomy appliance as defined in claim 5 wherein said mesh sheath has pores of between 600 and 750 microns in diameter.

7. The ostomy appliance as defined in claim 5 wherein said filament spirals in and through said mesh sheath for substantially the entire length of said sheath.

* * * * *